United States Patent [19]
Markert et al.

[11] Patent Number: 6,146,626
[45] Date of Patent: Nov. 14, 2000

[54] DEFINED ENZYME MIXTURES FOR OBTAINING CELLS AND TREATING WOUNDS

[75] Inventors: Claus Otto Markert, Schifferstadt; Hans Thom, Limburgerhof; Jürgen Weymann, Bad Dürkheim; Wolfgang Zahn, Altrip, all of Germany

[73] Assignee: Knoll Aktiengesellschaft, Ludwigshafen, Germany

[21] Appl. No.: 08/913,396

[22] PCT Filed: Mar. 12, 1996

[86] PCT No.: PCT/EP96/01044

§ 371 Date: Sep. 16, 1997

§ 102(e) Date: Sep. 16, 1997

[87] PCT Pub. No.: WO96/28543

PCT Pub. Date: Sep. 19, 1996

[30] Foreign Application Priority Data

Mar. 16, 1995 [DE] Germany .......... 195 09 584
Sep. 7, 1995 [DE] Germany .......... 195 32 906

[51] Int. Cl.$^7$ .......... A61K 38/48; A61K 38/46; C12N 9/48
[52] U.S. Cl. .......... 424/94.63; 424/94.1; 424/94.66; 435/183; 435/212; 435/218; 435/219
[58] Field of Search .......... 435/212, 218, 435/219, 183; 424/94.1, 94.63, 94.66

[56] References Cited

U.S. PATENT DOCUMENTS

| | | | |
|---|---|---|---|
| 4,968,614 | 11/1990 | Takiguchi et al. | 435/172.3 |
| 5,162,205 | 11/1992 | Takiguichi et al. | 435/68.1 |

FOREIGN PATENT DOCUMENTS

| | | |
|---|---|---|
| 0244189 | 11/1987 | European Pat. Off. . |
| 94-00580 | 1/1994 | WIPO . |
| 96-00283 | 1/1996 | WIPO . |

OTHER PUBLICATIONS

Catalogue of Bacteria and Phages (p. 59) 17$^{th}$ Edition ATCC 1989.
Int. J. of Artifical Organs/ vol. 16, No. 9, 1993/pp. 677–681, Gerlach et al.
ATLA 22, 231–241, 1994, Blaauboer et al., The Practical Applicability of Hepatocyte . . . .
Methods in Enzymology, vol. 82, 453–471, Peterkofsky Bacterial Collagenase.
Ann Rev. Biochem. 1980, 40:1063–78, Harper.
J. of Vascular Surgery, Suggs et al., Enzymatic Harvesting of Adult Human Saphenous Vein . . . , 205–213.
J. of Biological Chem., vol. 246, No. 21, Nov. 10, 6522–6531, 1971, Cuatrecasas.
Experimental Cell Res., 149 (1983) 227–236, Hefley et al.
Diabetologia (1992) 35:735–742, Wolters et al.
Laboratory Tech. in Biochemistry and Molecular Biology, vol. 21, Berry et al. 1991.
J. of Cell Bio., vol. 43, 1996, Berry et al.506–520.
Wolfgang Grassmannu Arnold Nordwig, Bd. 322(1960) 267–273.
Bio. Pharm., vol. 47, No. 12, pp. 2193–2200, 1994, Sandker et al.
Cancer Res. 44, 1671–1675, Apr. 1984, Hoover et al.
Diabetologia, Springer–Verlag 1994, A216 Third Joint Dutch In Vitro Tox., ATLA 21, 466–468, 1993, Olinga et al.
Biochem. 1984, 23, 3085–3091, Bond et al.
Biol. Chem. Hoppe–Seyler, vol. 375, pp. 89–92, Feb. 1994, Ullmann et al.
Preparation of Isolated Rat Liver Cells, Chapter 4, Meth. Cell Biol. 73, 29–83 1976.
Culture of Human Endothelial Cells, Jaffe et al., 2745–2756 Journal Clinical Invest. vol. 52 Nov. 1973.
Cell Biology and Toxicology, vol. 7, No. 4, 1991, 315–325, Eisenmann–Tappe et al.
Enzymatic Debridement of Third–Degree . . . Webster et al., 602–608 vol. 83 1962.
Analytical biochemistry 112, 70–75, (1981) Jamall et al.
Bond et al Biochem 1984, 23 , pp. 3085–3091, "Characterization of the Individual Collagenases from Clostridium".

*Primary Examiner*—Herbert J. Lilling
*Attorney, Agent, or Firm*—Keil & Weinkauf

[57] ABSTRACT

The invention relates to the use of mixtures of defined composition of purified enzymes from *Clostridium histolyticum* for obtaining, in a reproducible, standardized manner, cells or tissue fragments from human or animal tissues, and to these enzymes and mixtures thereof; in addition it relates to the direct or indirect medical use of these enzymes, alone or as ingredient of mixtures, eg. in wound treatment.

5 Claims, No Drawings

DEFINED ENZYME MIXTURES FOR OBTAINING CELLS AND TREATING WOUNDS

This application is a 371 of PCT/EP96/01044 filed Mar. 12, 1996.

The present invention relates to the use of defined mixtures of purified enzymes from *Clostridium histolyticum* for obtaining, in a reproducible, standardized manner, cells or tissue fragments from human or animal tissue and to the use of these purified enzymes for wound treatment.

Methods for isolating cells from tissues ought to be reproducible and guarantee minimum damage to the cells obtained. In general, collagenase-containing preparations with an indefinite composition from *Clostridium histolyticum* are used for this purpose, but these aims are not reliably achieved therewith. The use of other enzyme preparations or nonenzymatic methods is not customary or provides only poor isolation results (1), (9).

The collagenase-containing preparations (2) normally used and recommended for use are obtained from filtrates of cultures of the bacterial strain *Clostridium histolyticum* and, besides various collagenases and proteases (3a), (3b), also contain cleavage products of these enzymes formed by proteolysis, and other constituents, some of which have injurious effects and are unknown.

According to the present state of knowledge, it is not possible with a single enzyme from *Clostridium histolyticum* to obtain viable cells in good yield. On the contrary, it is necessary for various enzymes from this bacterium to act together in order to achieve efficient tissue breakdown. However, the ratio of the amounts of enzymes necessary for this has not hitherto been disclosed. Nor have defined mixtures of enzymes from *Clostridium histolyticum* been available for the user.

Based on the problem described, various research groups have attempted to employ purified enzymes for isolating cells from tissues. However, this has never entailed use of pure enzymes and thus any clearly defined mixtures either.

Suggs et al. (4) isolated human vein endothelial cells using a mixture composed of a purified collagenase fraction and purified trypsin from beef pancreas. The enriched collagenase fraction employed did not, however, have a defined content of the various enzymes and still contained, for example, small amounts of clostripain. The isolation result was not significantly different from that obtained on use of collagenase-containing preparations with an indefinite composition. It was not possible to achieve satisfactory tissue disintegration using single components of the mixture. However, the use of trypsin for cell isolation is not without problems because this proteolytic enzyme attacks membrane proteins. Thus, for example, there is an adverse affect on insulin binding to liver membranes and to adipocytes (5).

Hefley (6), (7) employed mixtures of purified collagenase fractions (6) to isolate bone cells from the cranium of mice. Earlier (7), the author reported that it is possible to employ a mixture of a purified collagenase fraction together with a neutral protease for successful isolation of these cells. However, in both studies there was use of eluates from column fractionations whose content of various collagenases differing in their substrate specificity, and of other components, was unknown.

Wolters et al. (8) used mixtures of neutral protease and "collagenase type VII" supplied by Sigma, although it is unknown which types and amounts of various collagenases this contained, to isolate islet cells from the rat pancreas. In addition, it had a small content of clostripain und "nonspecific protease". The neutral protease was employed in a highly purified form. Mixtures of the two said components afforded good yields of viable islet cells.

The present invention relates to the individual enzymes collagenase HP, collagenase AZ and elastase in high purity, and to mixtures thereof.

Collagenase HP has a specific activity of at least 20 U/mg, preferably at least 50 U/mg, in the assay of Graβmann and Nordwig (11) with the synthetic hexapeptide Z-Gly-Pro-Gly-Gly-Pro-Ala as substrate. For pharmaceutical purposes it preferably has a specific activity of 100 U/mg or more.

Collagenase AZ has a specific activity of at least 10 U/mg, preferably at least 30 U/mg, in the assay of Mandl et al. (12) using azocoll as substrate. For pharmaceutical purposes it preferably has a specific activity of 50 U/mg or more.

Elastase has a specific activity of at least 2 U/mg, preferably at least 5 U/mg, in the assay with elastin from bovine neck ligament as substrate. For pharmaceutical purposes it preferably has a specific activity of 12 U/mg or more.

The invention furthermore relates to the use of a mixture of collagenase HP and elastase, with or without the addition of collagenase AZ and/or clostripain, to isolate cells or tissue fragments from human or animal tissue.

The invention furthermore relates to the direct or indirect use of these enzymes, alone or as ingredient of mixtures, for medical applications, eg. in wound treatment.

For use for tissue disintegration, the mixtures can, for example, be packed in lyophilized form in vials in amounts sufficient for disintegration of a single rat liver (about 9–11 g wet weight of the organ).

Suitable mixtures are those comprising at least two of the purified enzymes collagenase HP (50–300 U; preferably 70–170 U) and elastase (5–70 U, preferably 10–25 U) with or without addition of collagenase AZ (1–20, preferably 2–8 U) and/or clostripain (10–280 U, preferably 20–50 U). The stated numbers indicate the amounts present in one unit of the mixture—for example in a vial.

The purity criterion for the enzymes used is the specific activity thereof in each case and demonstration of their homogeneity in the electrophoretic methods normally used for this purpose (SDS gel electrophoresis, isoelectric focusing and electrophoresis on agarose gel). The specific activity of the purified enzymes reaches values which are up to 100 times that in the starting material.

Purified enzymes with the following specific activities are used to prepare the mixtures: collagenase HP with a specific activity of at least 20 U/mg, elastase with at least 2 U/mg, collagenase AZ with at least 10 U/mg and clostripain with at least 10 U/mg.

The mixtures are, by reason of their defined composition of synergistically acting collagenolytic, and elastinoloytic and proteolytic enzymes, particularly suitable for non-damaging and efficient isolation of cells or tissue fragments from animal and human tissues.

It is a considerable advantage that time-consuming and costly testing of batches is no longer necessary because the preparation starts from purified enzymes with known properties in each case. This dispenses with the work needed for functional characterization of the cells, or at least it becomes less. For these reasons, the number of animal experiments can in many areas be reduced.

The use of less well purified enzymes, or use of enzymes with lower specific activity, usually leads to poorer yields of cells in said applications, and is furthermore associated with the customary problems of lack of reproducibility of the isolation result, lack of batch consistency and the presence of unknown constituents which may have adverse effects.

Many of the experimental results reported in the literature are difficult to interpret because of the breakdown of the enzymes occurring due to concomitant proteases during preparation, purification or characterization. Elucidation of the contribution of the individual enzymes to the experimental result in the isolation of cells has also been made difficult by the fact thatthe fragments produced from the collagenases, the elastase and the proteases in some cases retain their enzymatic activity. However, the extent to which the substrate specificities are changed thereby has not been elucidated. Moreover, many commercial collagenase-containing preparations sometimes contain only breakdown products of the original collagenases. Thus, in the prior art it was not possible either for the manufacturer of the preparations or for the user of cell isolation methods to standardize collagenase-containing preparations unambiguously.

The mixtures according to the invention of purified enzymes are suitable, because of their broad activity in breaking down tissues, for application to all human and animal tissue and cells, preferably tissue fragments and/or cells from:

the biliary tract, the blood system, glands, the vascular system, the brain, the skin, the heart, the intestine, the islets of Langerhans, the liver, the lung, the stomach, the spleen, muscles, the unbilical cord, nerves, the kidney, the pancreas, the spinal cord, the thyroid, the terminal ileum, tumor tissue, the uterus, the digestive tract and the tongue.

The cells or tissue fragments isolated using the described mixtures are very particularly suitable for use in cell and tissue transplantation, and in gene therapy (eg. islets of Langerhans, islet cells, hepatocytesl tumor cells, adipocytes), in immunotherapy or in wound healing.

A particularly important use of the mixtures according to the invention is in the isolation of hepatocytes, islet cells, endothelial cells, epithelial cells, adipocytes, oocytes and tumor cells. Standardization and improvement of the methods in these areas of application is particularly advantageous.

For example, a mixture with a defined composition of 2 collagenases which differ in substrate specificity and an elastase has proven outstandingly suitable for the isolation of hepatocytes from rat liver (Use Examples A, D, E) and human liver (Use Example F), of bile duct epithelial cells from rat livers (Use Example G), of endothelial cells from human umbilical cords (Use Examples H), and for isolating tumor cells from human tumors (Use Example I) and islet cells from pig pancreas (Use Example J).

Compared with the best collagenase-containing enzyme preparations of undefined composition, the isolation result achieved is better or at least equally good.

The mixtures according to the invention can be used as substitute for all normally used collagenase-containing preparations because they have the components necessary for tissue disintegration. The disadvantages of the collagenase-containing preparations used to date are avoided, inter alia because of the consistent composition of the mixtures.

An important area of use of said mixtures is for obtaining, in a reproducible, standardized manner, hepatocytes from the liver by the accepted method of Berry and Friend (9), (10), in which use has been made hitherto of collagenase-containing enzyme preparations of undefined composition, and for better obtaining, by using said prior art mixtures, islet cells in intact form from pancreatic tissue.

Another main area of application is in wound healing. For this the enzymes are used in as high a purity as possible.

I. Preparation and characterization of the enzymes from *Clostridium histolyticum*

1. Collagenase HP a. Preparation

Fractional Precipitation of Proteins with Ammonium Sulfate

All the operations in the enzyme purification were carried out at 4–8° C.

200 g of crude collagenase were dissolved in 3 l of water, and initially 680 g of powdered ammonium sulfate were introduced into the resulting solution. The protein precipitate A1 was removed by centrifugation; a further 420 g of ammonium sulfate were added to the supernatant. This precipitated protein fraction A2 was removed by centrifugation, and the precipitate was dissolved in 1 l of water and dialyzed against water. It was then concentrated to about 100 ml through an ultrafiltration membrane (exclusion limit 10,000 Da). The concentrate was then lyophilized. The resulting powder of protein fraction A2 contained collagenase HP and collagenase AZ as main components.

Chromatographic separation of HP and collagenase AZ by metal chelate affinity chromatography Collagenase HP and collagenase AZ were separated by chromatography on $Zn^{2+}$-loaded chelating Sepharose 6 B. This was done by packing this material to a height of 70 cm in a column (5×100 cm) and equilibrating with starting buffer (500 mM sodium acetate+20 mM calcium acetate, pH 8.0). Then about 1.2 g of protein fraction A2, dissolved in 15 ml of starting buffer whose pH had been corrected to 8.4 with TRIS [tris(hydroxymethyl)aminomethane], were loaded onto the column, and various constituents of protein fraction A2 were washed out of the column with starting buffer. In the subsequent elution with buffer A (500 mM sodium acetate+20 mM calcium acetate, corrected to pH 6.3 with acetic acid), initially collagenase AZ, and then collagenase HP, was collected in separate fractions.

The two separated fractions of collagenase HP and collagenase AZ enzymes were concentrated to 50–100 ml using an ultrafiltration membrane (exclusion limit 10,000 Da), then dialyzed against water and again concentrated to about 10 ml through an ultrafiltration membrane (exclusion limit 10,000 Da).

Final Purification of Collagenase HP

The final purification of collagenase HP took place on a Mono Q anion exchanger (HR 10/10, Pharmacia) using a Pharmacia FPLC apparatus. This was done by loading onto the column, which had been been equilibrated with buffer B (20 mM TRIS/HCl pH 7.5), a mixture of 1 ml of buffer B and 2 ml of the fraction containing collagenase HP from the previous chromatography step.

After washing with buffer B, collagenase HP was eluted from the column in purified form using buffer C (20 mM TRIS/HCl+200 mM NaCl, pH 7.5).

b. Properties

Collagenase HP was given the designation "HP" because of its property of breaking down the hexapeptide Z-Gly-Pro-Gly-Gly-Pro-Ala particularly well. It is therefore suitable for specific detection of the activity. Collagenase HP has the characteristic that it is able to convert denatured collagens such as gelatin or azocoll to only a small extent. However, it attacks bovine tendon collagen and cleaves, with a high conversion, the synthetic peptides mentioned in Example 2b between glycine and glycine or between any amino acid and glycine.

It should be particularly emphasized that collagenase HP together with the collagenase AZ (vice versa, ie. thus also any mixtures of at least collagenase HP and AZ) has a superadditive effect on the breakdown of native collagen. The synergistic effect in vitro is also important on use for tissue disintegration (eg. Use Example G).

The maximum specific activity of collagenase HP in the assay with the synthetic substrate Z-Gly-Pro-Gly-Gly-Pro-Ala is 146 U/mg (11). This corresponds to an increase by about 100-fold in the specific activity compared with the starting material.

The collagenase HP purified in this way forms only a single band both in SDS gel electrophoresis and in isoelectric focusing and electrophoresis on agarose gel.

Its molecular weight determined by SDS electrophoresis is 106,000 Da. Its isoelectric point is pr 5.8–6.0.

2. Collagenase AZ a. Preparation

All the operations in the enzyme purification were carried out at 4–8° C. The first two purification steps for collagenase AZ (fractional protein precipitation and metal chelate affinity chromatography) are described under 1.

Final Purification of Collagenase AZ

The final purification of collagenase AZ was carried out on the Mono Q anion exchanger (HR 10/10, Pharmacia) with the assistance of the Pharmacia FPLC apparatus. This was done by loading a fixture of 1 ml of buffer D (20 mM calcium acetate, pH 7.2) and 1 ml of the fraction containing collagenase AZ (from the metal relate affinity chromatography described above) onto the column which had been equilibrated with buffer D.

After washing with buffer D, the collagenase AZ was eluted from the column with buffer E (20 mM calcium acetate, pH 5.0).

b. Properties

Collagenase AZ was given the designation "AZ" because of its property of breaking down the substrate azocoll particularly well. It has the characteristic of efficiently converting denatured collagens such as gelatin or azocoll, but also bovine tendon collagen. However, it is not able to attack small synthetic peptides such as 2-furanacryloyl-Leu-Gly-Pro-Ala, 4-phenylazobenzyloxycarbonyl-Pro-Leu-Gly-Pro-Arg and Z-Gly-Pro-Gly-Gly-Pro-Ala.

The maximum specific activity of collagenase AZ in the assay developed by Mandl et al. (12) using azocoll as substrate is 82 U/mg. This corresponds to an increase in its specific activity by about 80-fold compared with the starting material.

The collagenase AZ purified in this way forms only a single band both in SDS gel electrophoresis and in isoelectric focusing and electrophoresis on agarose gel.

Its molecular weight determined by SDS gel electrophoresis is 111,000 Da. Its isoelectric point is pH 5.9–6.1.

3. Elastase a. Preparation

All the operations in the enzyme purification were carried out at 4–8° C.

The first step in the elastase purification took place by protein precipitation with ammonium sulfate as described under 1.a.

The protein precipitate A1 is dissolved in 1 l of water, concentrated to about 170 ml through an ultrafiltration membrane (exclusion limit 10,000 Da) and dialyzed against 0.1 mM calcium acetate solution. The enzyme solution was subsequently concentrated anew to about 50 ml through an ultrafiltration membrane (exclusion limit 10,000 Da) and then lyophilized.

The final purification took place by gel chromatography on SEPHADEX G100 or G200 (Pharmacia).

b. Properties

Elastase has the characteristic that it is able to break down elastin with a high conversion. Its specific activity (see 3.c.) was 18 U/mg. This corresponds to an increase in its specific activity by about 80-fold compared with the starting material.

The elastase purified in this way forms only a single band both in SDS gel electrophoresis and in isoelectric focusing and electrophoresis on agarose gel.

The molecular weight of elastase determined by SDS electrophoresis is 35,000 Da.

c. Activity Determination

The enzyme activity was determined using the substrate elastin.

20 mg of finely powdered elastin from bovine neck ligament (Sigma) were preincubated in 0.4 ml of buffer (50 mM TRIS/HCl+10 mM calcium acetate, pH 7.2) shaking in a water bath at 37° C. for 5 min. The reaction was then started by adding elastase, dissolved in 0.1 ml of buffer, and shaking was continued at 37° C. for 10 min (excursion 25 mm, rate 150 min$^{-1}$). Then 3.5 ml of ice-cold water were added, and the unreacted elastin was immediately removed on a filter. The extinction E of the filtrate was measured in a spectrophotometer at a wavelength of 280 nm. The blank was the extinction $E_B$ obtained in an experiment carried out in the same way but in which the elastase solution had been added to the mixture only after removal of the elastin. The extinction $E_B$ of this filtrate was then likewise determined at 280 nm.

The elastase activity is expressed in units [U]. 1 U is defined as the enzyme activity which, under the given experimental conditions, dissolves 1 mg of elastin per minute. The dissolved amount of elastin was determined in the filtrate from the assay mixture by measuring the extinction at 280 nm.

The specific activity was calculated by the following formula:

$$U/mg = \frac{\Delta E \times F \times \text{assay volume} \times \text{dilution factor}}{\min \times \text{mg of elastase in the assay mixture}}$$

$\Delta E = E - E_B$ $F = 1.376$

The factor F is determined by completely dissolving 10 mg of elastin of a particular batch using elastase, and measuring the corresponding extinction difference $\Delta E$. Multiplication of this factor F by extinction difference $\Delta E$ gives the amount of elastin dissolved in milligrams per ml of assay mixture.

4. Clostripain a. Preparation

Clostripain was isolated by the method described by Ullmann and Jakubke (14).

Its specific enzyme activity was determined using the synthetic substrate α-N-benzoyl-L-arginine ethyl ester (=BAEE) after previous activation of the clostripain solution with 2 mM 1,4-dithioerythritol solution for 3 hours (15). It was about 83 U/mg.

b. Properties

The thiol protease clostripain has the characteristic that it cleaves specifically behind the amino acid L-arginine in polypeptide chains and in synthetically prepared substrates.

Its molecular weight determined by SDS electrophoresis is 55,000 Da.

II. Use Examples

The following Examples A–J show the particular suitability of some mixtures of the purified enzymes for isolating cells and tissue fragments from animal and human tissue. Examples K and L show the suitability of the purified enzymes for use in wound healing.

The invention is not restricted to these Use Examples.

EXAMPLE A

Isolation of hepatocytes from the liver using mixtures of three enzymes

Hepatocytes were isolated by the standard method of Berry and Friend (9) and the modifications by Seglen (16). Wistar rats (200–280 g) were anesthetized by i.p. injection of Nembutal (35 mg of pentobarbital/kg of body weight). After the abdominal cavity had been opened, the portal vein was cannulated and, under constant hydrostatic pressure (12 cm column of water, variable flow rate), the following carbogen-aerated solutions with a pH of 7.4±0.05 were infused at 36–36.8° C. after opening of the inferior vena cava:

Perfusion:

| | |
|---|---|
| 1. 5 min | about 100 ml of cell buffer without $Ca^{2+}$ |
| 2. 5 min | about 100 mL of cell buffer without $Ca^{2+}$, with EGTA (0.42 mM) |
| 3. 8 min | about 200 ml of cell buffer without $Ca^{2+}$ |
| 4. 5–30 min | about 100–600 ml of cell buffer in which the lyophilized mixtures of the purified enzymes had been dissolved. |

Cell buffer:

| | |
|---|---|
| 120.0 mM NaCl | 1.29 mM $CaCl_2$ |
| 5.50 mM D(+)-Glucose | 1.19 mM $KH_2PO_4$ |
| 4.81 mM KCl | 1.20 mM $MgSO_4$ |
| 15.0 mM $NaHCO_3$ | 10.0 mM HEPES |

Carbogen: Gas mixture consisting of 95% $O_2$ and 5% $CO_2$ (v/v).

The enzyme mixture was a lyophilizate of 130 U of collagenase HP, 5 U of collagenase AZ and 21 U of elastase, which was dissolved in 87.5 ml of cell buffer.

The perfursion was stopped when the liver tissue became soft. After detachment of the Glisson's capsules, the hepatocytes were shaken out of the liver tissue and filtered through a screen fabric (100 μm mesh width). After the filtration, the cells were shaken in a water bath at 37° C. under a carbogen atmosphere for 20 min. Intact hepatocytes were collected by three 2-minute centrifugation steps in cell buffer at 50 times the acceleration due to gravity. The supernatant, which mainly contained dead cells, was discarded after each centrifugation. The content of vital hepatocytes, pairs of hepatocyte cells or multicellular aggregates of hepatocytes was determined by microscopy in a Burker counting chamber after resuspension of the resulting cell pellet (staining with 0.08% strength trypan blue, 2 min).

RESULT

One series of experiments (n=4) using the described enzyme mixture resulted in cell suspensions which contained on average 88.7% vital cells, with a yield of $360 \times 10^6$ cells per liver.

Comparative experiments with a collagenase-containing preparation of undefined composition with particularly high specific collagenolytic activity led to severe cell damage and only 72.5% vital cells (n=4).

EXAMPLE B

Isolation of Hepatocytes from the Liver using a Mixture of two Enzymes

The procedure was similar to Example A but using the following enzyme mixture: 60 U of collagenase HP and 3 U of elastase. The resulting cell suspensions contained on average 90.5% vital cells, with a yield of $263 \times 10^6$ cells (n=2).

EXAMPLE C

Isolation of Hepatocytes from the Liver using a Mixture of Four Enzymes

The procedure was similar to Example A but using the following enzyme mixture: 30 U of collagenase HP, 5 U of collagenase AZ, 3 U of elastase and 16 U of clostripain.

The resulting cell suspensions contained on average 83% vital cells, with a yield of $232 \times 10^6$ cells (n=2).

EXAMPLE D

Wide-ranging validation of the result of isolation of hepatocytes from the rat liver with a mixture of three enzymes in 4 different laboratories by comparison with collagenase-containing preparations of undefined composition There are known to be small differences, which may, however, be important for the result of isolation of hepatocytes, in the method of cell isolation from laboratory to laboratory. In order to check, independently of the methodology used, the efficacy of the mixture mentioned in Example A for cell isolation, a large number of hepatocyte isolations were carried out in 4 different laboratories.

The enzyme mixture used was a lyophilizate of 130 U of collagenase HP, 5 U of collagenase AZ and 21 U of elastase, which was in 87.5 ml of cell buffer (as in Example A).

The result of isolation of hepatocytes was measured by means of the following five parameters: 1. microscopic determination of the content of vital hepatocytes (as % of the total number of hepatocytes in the resulting cell suspension by the trypan blue exclusion test), 2. determination of the total number of isolated hepatocytes, 3. determination of the total number of isolated hepatocytes per gram of animal weight, 4. determination of the content of single cells (as % based on all aggregation forms in the resulting cell suspension, ie. compared with double and multiple aggregates of hepatocytes), and 5. establishment of the perfusion time with the collagenase solution necessary for successful tissue disintegration.

In these tests, the mixtures of enzymes according to the invention showed considerably more reproducible results than conventional preparations.

EXAMPLE E

Isolation of hepatocytes from rat liver using a mixture of 3 enzymes: retention of cell function In order to prove not only the suitability of the mixtures according to the invention with regard to the simple result of isolation of hepatocytes, but also with particular consideration of cell function, comparative cell isolations were carried out using a collagenase-containing preparation, which is particularly suitable for this purpose and is of undefined composition, on rat livers.

Hepatocytes were isolated by the standard method of Berry and Friend (9) and the modifications by Seglen (16).

The enzyme mixture used was a lyophilizate of 130 U of collagenase HP, 5 U of collagenase AZ and 21 U of elastase, which was dissolved in 87.5 ml of cell buffer for the isolation of hepatocytes from rat livers (as in Example A).

The simple result of isolation of rat hepatocytes was determined from the following parameters: content of vital cells by the trypan blue exclusion test, cell yield per g of liver, content of single cells (in %).

The quality of the resulting cell suspension was further characterized in respect of hepatocyte function (21, 22) by the following parameters: ATP content, energy charge (EC), lidocaine metabolism to monoethylglycine xylidide (MEGX), and uptake of cholyltaurine (($3\alpha,7\alpha,12\alpha$-trihydroxy-$5\beta$-cholan-24-oyl)-2-aminoethanesulfonic acid) at a substrate concentration of 21 $\mu$M.

No significant differences between the two collagenase-containing preparations were revealed in any of the parameters investigated.

It was thus possible to show that the hepatocytes isolated using an enzyme mixture according to the invention are completely intact not only according to assessment by the simple result of isolation but also according to assessment of various cell functions, eg. particular functions of differential substance transport, or particular metabolic activities of cytochrome P450-dependent enzymes of the hepatocytes.

EXAMPLE F
Isolation of Hepatocytes from Human Liver using a Mixture of 3 Enzymes Hepatocytes were isolated by the method of Berry and Friend (9) and the modifications by Seglen (16) using a biopsy perfusion technique (21).

The enzyme mixture used was a lyophilizate of 130 U of collagenase HP, 5 U of collagenase AZ and 21 U of elastase, which was dissolved in 50 ml of cell buffer.

The result of isolation of human hepatocytes was determined by the following parameters: content of vital cells by the trypan blue exclusion test and cell yield per g of liver.

It emerged that it is also possible with the mixtures according to the invention successfully to isolate hepatocytes from human livers with constant results (content of vital cells 85–90%).

EXAMPLE G
Isolation of Biliary Epithelial Cells from the Rat Liver

In one series of experiments (n=4), biliary epithelial cells were isolated from the rat liver by the method described in reference (18). This entailed, in a first step of tissue disintegration, initially hepatocytes being removed enzymatically from the tissue assemblage and, in a second step, biliary epithelial cells being isolated from the remaining tissue residues with trypsin.

The enzyme mixture for removing the hepatocytes was a lyophilizate of 130 U of collagenase HP, 5 U of collagenase AZ and 21 U of elastase, which was dissolved in 87.5 ml of cell buffer.

The proportion of vital epithelial cells in all the preparations was more than 95%, and the cell yield was 4–6×10$^6$ cells per liver (n=4). Use of the described enzyme mixture facilitated extraordinarily well the isolation of biliary epithelial cells from the remaining vessel system by means of trypsin, because the residual tissue obtained after the first step was virtually free of hepatocytes.

The problem with the methods hitherto used to obtain biliary epithelial cells was that the hepatocytes remaining in the cell suspension, and Kupffer cells and other types of cells were, as a rule, difficult to remove from the epithelial cells to be isolated.

Use of the described mixture of pure enzymes allows a clear saving of time and costs to be achieved because, compared with the method hitherto used, the disintegration of the liver tissue is unambiguously improved and virtually complete. This means that the desired removal of contaminating hepatocytes, which are normally present in large numbers, is successful.

EXAMPLE H
Isolation of Endothelial Cells from Human Umbilical Cord using a Mixture of 3 Enzymes Human endothelial cells from the umbilical vein were isolated by the method of Jaffe (17). This was done by halving the umbilical cords (20–30 cm long), filling them pairwise with the particular enzyme solution and incubating in an incubator at 37° C. with 5% $CO_2$ for 15 min. The detached cells were removed and maintained in primary culture for evaluation. The yield of live cells capable of division was determined after the nonadherent cells had been washed out after four days in culture.

The enzyme mixture was a lyophilizate of 130 U of collagenase HP, 5 U of collagenase AZ and 21 U of elastase, which was dissolved in 87.5 ml of cell isolation buffer.

The day after inoculation of the cells, the nonadherent cells (erythrocytes, macrophages, etc.) are washed out. The medium is changed on the fourth day. Confluence is usually reached no later than the eighth day after inoculation (>10$^5$ cells/cm$^2$). The confluent cell lawn comprises more than 95% endothelial cells as shown by FACS investigations with antibodies against factor VIII-related antigen (Von Willebrand factor) or two endothelial nonspecific surface antigens (EN-4, PAL-E) and with a fluorescent ligand of the scavenger receptor (dil-Ac-LDL).

The yield obtained with the abovementioned mixture of purified enzymes (n=2) exceeded that obtained with collagenase-containing enzyme preparations of undefined composition. The cell density after 4 days was 1.8×10$^4$ per cm$^2$. Use of methods disclosed hitherto results in a cell density which is distinctly below this. Confluence of the monolayer was reached at an earlier time (after only 5–6 days) on use of the abovementioned mixture.

On enzymatic isolation of the endothelial cells using the various enzyme preparations there was no rupture of the umbilical vein in any case. The removed cells were satisfactorily isolated. No cytotoxic manifestations were observed. Adhesion of endothelial cells was found after one hour.

The prepared cells were subjected to functional tests (endothelin production; LDH release) in the first passage. All the values from this were within the normal range. The cells were thus functionally indistinguishable from the results from control experiments in which cells had been isolated with collagenase-containing preparations of undefined composition.

The superiority of the mixture of purified enzymes employed is thus evident in the higher cell yield which is possible, faster development of the confluent monolayer, and optimal integrity of the isolated cells (cell structure and function).

Comparably good results were obtained in experiments in which the abovementioned enzyme mixture was replaced by other mixtures, eg. comprising collagenase HP and elastase, and mixtures of collagenase HP, collagenase AZ, elastase and clostripain.

EXAMPLE I
Isolation of Tumor Cells from Human Tumors using a Mixture of 3 Enzymes Tumor cells were isolated from human tumors by method (23).

The enzyme mixture used was a lyophilizate of 130 U of collagenase HP, 5 U of collagenase AZ and 21 U of elastase, which was dissolved in 28.4 ml of cell isolation buffer (Ringer lactate/PBS).

The result of isolation was determined by means of the content of vital cells by the trypan blue exclusion test and counting the lymphocyte cell count. Directly comparative cell isolations were carried out using the enzyme mixture according to the invention and a collagenase-containing preparation, which is very suitable for this purpose and is of undefined composition, on 4 different tumor tissues.

RESULT

The enzyme mixture according to the invention can be used very satisfactorily for isolating tumor cells from human tumors.

The result of isolation corresponds, within the range of experimental variations, to the result of isolation obtained with selected collagenase-containing preparations which are particularly suitable for tumor cell isolation and are of undefined composition.

Since, according to the results presented here, successful disintegration of a wide variety of connective tissue structures in human tumor tissue is possible with the enzyme mixture according to the invention, always attaining or improving the prior art (result of isolation, quality of the isolated cells, and retention of methodological variables), the suitability of the enzyme mixtures according to the invention for disintegration also of other animal and human tissues can be assumed.

EXAMPLE J
Isolation of Islet Cells from Pig Pancreas using a Mixture of 3 Enzymes To isolate islet cells from pig pancreas, the well-known preparative method of Ricordi was used, introducing some essential modifications (24), inter alia to improve monitoring of the result of isolation. In this case, the collagenase solution acts for a lengthy period, under particularly well-standardized conditions, on the pancreatic tissue after infusion through the pancreatic duct. The islets which have been detached are continuously discharged into a reservoir at a lower temperature and, after the end of the distintegration, the islets which have already been partly freed of their matrix in the pancreatic tissue are completely detached and isolated by applying gentle mechanical treatment.

Isolation of islet cells from the pancreas makes extremely high demands on a collagenase-containing preparation because the bases for successful isolation of intact islets from the pancreas are insufficiently well known.

The suitability of a defined enzyme mixture according to the invention is proved by way of example below. This means that, with this tissue type too, the suitability for successful tissue disintegration with the aim of isolating large native cell aggregates (islets of Langerhans) is also applicable to the use of pancreases from other species (eg. human pancreas). These prospects are supported by experiences which generally assess the isolation of islets from pig pancreas a's more difficult than from the pancreases of other species. For example, it is known (25) that islets from pig pancreas are very easily disintegrated to smaller, unwanted fragments by conventionally used collagenase-containing preparations of undefined composition. This is explained by the particular properties of the cells in islet aggregates, which have many protease-sensitive cell-cell contacts, both between endocrine and exocrine cells and between endocrine cells and the islets. Thus the aim of an improved isolation method can only be to obtain larger numbers of intact islet cell aggregates, and fragmentations to aggregates <100 µm should occur to only a smaller extent.

The enzyme mixture used in this use example for the isolation of islets from pig pancreas was a lyophilizate of 130 U of collagenase HP, 5 U of collagenase AZ and 21 U of elastase, which was dissolved in 10 ml of isolation buffer. Deoxyribonuclease (0.4 mg/10 ml, 440 Kunitz units/mg, SIGMA) was routinely added to this solution.

The result of isolation can be determined on the basis of the size distribution of the resulting intact cell aggregates and other usual parameters.

A particular advantage of the use of the enzyme mixture according to the invention can be stated to be that the proportion of free islets above 100 µm which can be obtained is more than with conventional preparations.

EXAMPLE K
Experimental Investigations on Wound Treatment in vivo

Collagenases are responsible in wound healing for efficient removal of necrotic tissue, recruitment of cells in the region of the wound and transformation of the extracellular matrix.

In an experimental in vivo model of wound cleansing described by Webster (19), the histolytic property of the purified enzymes was examined in rats.

An increased rate of breakdown, depending on the amount of the purified enzymes applied to the third degree burn wound, of the denatured tissue was observed within the first 16 hours. The enzymes were applied singly or in combination with other enzymes. The best results were obtained on application of a mixture of collagenase HP (3–48 U/cm$^2$, preferably 16 U/cm$^2$), collagenase AZ (0.2–3 U/cm$^2$, preferably 1 U/cm$^2$) and elastase (1–12 U/cm$^2$, preferably 3 U/cm$^2$). In this case, the scab was almost completely broken down in 8 of 15 animals, and partial breakdown was achieved in 6 of 15 animals. In the latter cases it was extremely easy to remove the necrotic tissue mechanically, in contrast to the control.

After a shorter application time of 4 hours using the same amounts, a softening of the necrotic material was found, and in all cases it was possible to remove the scab satisfactorily (in contrast to the control).

Besides this mixture, it was possible to use other mixtures successfully too, eg. those of collagenase HP (3–48 U/cm$^2$) and elastase (1–12 U/cm$^2$).

EXAMPLE L
Experimental Investigations on Wound Treatment in vitro

The results obtained on the effect in breaking down necrotic tissue (Example K) were characterized further in an in vitro model. The release of 4-hydroxyproline (20) was determined after 2, 4, 6 and 24 h of collagenase HP, collagenase AZ and/or elastase acting on the scab from the burn wound mentioned in Example K in a shaken buffer solution.

The activities of the purified enzymes employed were identical to the relative activity in an effective comparative amount of a collagenase-containing preparation. In this experimental simplification, the respective contribution to the release of hydroxyproline by the other components in the collagenasecontaining preparation is ignored.

On use of the purified enzymes there was in all cases found to be a release, with a clear dependence on the time, of amounts of hydroxyproline comparable to the use of a corresponding amount of collagenase-containing preparation.

According to these results, the enzymes and enzyme mixtures purified according to the invention can also be used in areas of therapy such as in wound treatment or for treating keloids or fibroses. They can be applied externally or injected.

REFERENCES

1) Gerlach J. C., Brombacher J., Courtney J. M. and Neuhaus P. (1993) Int. J. Artif. Organs 16(9), 677–681
2) Blaauboer B. J. , Boobis A. R., Castell J. V., Coecke S., Groothuis G. M. M., Guillouzo A., Hall T. J. , Hawksworth G. M., Lorenzon G., Miltenburger H. G., Rogiers V, Skett P., Villa P. and Wiebel F. J. (1994) ATLA 22, 231–241
3a) Peterkowski B. (1982) Methods Enzymol. 82, 453–471
3b) Harper E. (1980) Ann. Rev. Biochem. 1063–1078
4) Suggs W., van Wart H. and Sharefkin J. B. (1992) J. Vasc. Surg. 15, 205–213
5) Cuatrecasas P. (1971) J. Biol. Chem. 246, 6522–6531
6) Hefley T. J. (1987) J. Bone Mineral Res. 2 (6), 505–516
7) Hefley T. J. , Stern P.H. and Brand J. S. (1983) Exp. Cell Research 149, 227–236
8) Wolters G. H. J, Vos-Scheperkeuter G. H., van Deijnen J. H. M and van Schilfgaarde R. (1992) Diabetologia 35, 735–742
9) Berry, M. N. , Edwards, A. M. and Barritt, G. J. (1991) In: Isolated hepatocytes: Preparation, properties and applications. (Burdon, R. H., van Knippenberg, P. H., Eds. ) Elsevier, Amsterdam, 1991
10) Berry, M. N. and Friend, D. S. (1969) J. Cell. Biol. 43, 506–520
11) Grafmann W. and Nordwig A. (1960) Hoppe-Seyler's Z. Physiol. Chem. 322, 267–272
12) Mandl I., MacLennan J. D., Howes E. L., DeBellis R. H. and Sohler A. (1953) J. Clin. Invest. 32, 1323–29
14) Ullmann D. and Jakubke H. -D. (1994) Biol. Chem. Hoppe-Seyler 375, 89–92
15) Emod I. and Keil B. (1977) FEBS Lett. 77, 51–66
16) Seglen P. O. (1976) Methods Cell. Biol. 13, 29–83
17) Jaffe E. A., Nachman R. L., Becker C. C. and Minick C. R. (1973) J. Clin. Invest. 52, 2745–56
18) Eisenmann-Tappe I., Wizigmann S. and Gebhardt R. (1991) Cell Biol. Toxicol. 7 (4), 315–325
19) Webster M. E., Altieri P. L., Conklin D. A., Berman S., Lowenthal J. P. and Gochenour R. B. (1962) J. Bacteriol. 83, 602–608
20) Jamall I. S., Finelli V. N. and Que Hee S. S. (1981) Anal. Biochem. 112, 70–75
21) Sandker G. W., Weert B., Olinga P., Wolters H., M. J. H. Slooff, D. K. F. Meijer and G. M. M. Groothuis (1994), Biochem. Pharmacol. 47, 2193–2200
22) Olinga P., Merema M. T., Meijer D. K. F., Slooff M. J. H. and Groothuis G. M. M. (1993) ATLA 21, 466–468
23) Hoover H. C. Jr., Surdyke M., Dangel R. B., Peters L. C. and Hanna M. G. Jr. (1984) Cancer Research 44, 1671–1675
24) Schrezenmeir J., Walz S., Marx S and Laue C., Diabetologia (1994) 37 [Suppl 1] A216
25) Ricordi C., Socci C., Davalli A. M., Staudacher C., Vertova A., Baro P., Freschi M., Gavazzi F., Bertuzzi F., Pozza G. and Di Carlo V. (1990) Horm. Metab. Res. Suppl. 25, 26–30

We claim:

1. An enzyme mixture obtainable from *Clostridium histolyticum*, which comprises
    a) a collagenase which has a specific activity of at least 20 U/mg in the assay of Nordwig and Strauch with the synthetic hexapeptide Z-Gly-Pro-Gly-Gly-Pro-Ala a s substrate, which is able to convert denatured collagens, to only a small extent but attacks bovine tendon collagen, whose molecular weight determined by SDS gel electrophoresis is 106,000 Da, and which has an isoelectric point at pH 5.8 to 6.0,
    b) a collagenase which has a specific activity of at least 10 U/mg in the assay of Mandl et al., using azocoll as substrate, which can efficiently convert denatured collagens, but also bovine tendon collagen, but is not able to attach small synthetic proteins whose molecular weight determined by SDS gel electrophoresis is 110,000 Da, and which has an isoelectric point at pH 5.9 to 6.1, and
    c) elastase which has a specific activity of at least 2 U/mg in the assay with elastin from bovine neck ligament as substrate and whose molecular weight determined by SDS electrophoresis is 35,000 Da.

2. The enzyme mixture of claim 1, further comprising the thiol protease clostripain.

3. A method for isolating cells or tissue fragments from human or animal tissue which comprises applying an active amount of an enzyme mixture comprising an enzyme a), an enzyme b) and an enzyme c) as defined in claim 1 to the human or animal tissue.

4. The method of claim 3, wherein the enzyme mixture further comprises the thiol protease clostripain.

5. A method for treating wounds or disorders associated with a change in collagen metabolism which comprises applying an active amount of an enzyme mixture comprising an enzyme a), an enzyme b) and an enzyme c) as defined in claim 1 to the human or animal tissue.

* * * * *